United States Patent
Watanabe et al.

(10) Patent No.: US 6,821,410 B2
(45) Date of Patent: Nov. 23, 2004

(54) BIOSENSOR AND METHOD OF SUBSTRATE QUANTIFICATION

(75) Inventors: Motokazu Watanabe, Katano (JP); Miwa Hasegawa, Nara (JP); Tomohiro Yamamoto, Hirakata (JP); Toshihiko Yoshioka, Hirakata (JP); Shiro Nankai, Hirakata (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 400 days.

(21) Appl. No.: 10/084,937

(22) Filed: Mar. 1, 2002

(65) Prior Publication Data
US 2002/0134676 A1 Sep. 26, 2002

(30) Foreign Application Priority Data
Mar. 7, 2001 (JP) .................. 2001-063083

(51) Int. Cl.⁷ .......................... G01N 27/327
(52) U.S. Cl. .............. 205/777.5; 204/403.1; 204/403.14
(58) Field of Search ........... 435/11, 19; 204/403.04, 204/403.05, 403.09, 403.1, 403.12, 403.14; 205/777.5, 778

(56) References Cited

U.S. PATENT DOCUMENTS

| | | |
|---|---|---|
| 3,884,784 A | 5/1975 | Goodhue et al. |
| 4,378,429 A | 3/1983 | Modrovich |
| 4,810,642 A | 3/1989 | Aoyama et al. .............. 435/28 |
| 5,192,415 A | 3/1993 | Yoshioka et al. ......... 204/403.08 |
| 5,268,269 A | 12/1993 | Rothe et al. .................. 435/11 |
| 5,288,636 A * | 2/1994 | Pollmann et al. ......... 204/403.14 |
| 5,434,055 A | 7/1995 | Jernigan ...................... 435/11 |
| 5,627,075 A | 5/1997 | Bateson ........................ 436/8 |
| 5,964,993 A * | 10/1999 | Blubaugh et al. ........ 204/403.09 |
| 6,042,714 A | 3/2000 | Lin et al. ...................... 205/782 |
| 6,258,229 B1 * | 7/2001 | Winarta et al. .......... 204/403.04 |

FOREIGN PATENT DOCUMENTS

| | | | |
|---|---|---|---|
| EP | 0 091 026 | 10/1983 | |
| EP | 0735363 A1 * | 10/1992 | ......... G01N/27/327 |
| EP | 0 636 879 A2 | 2/1995 | ......... G01N/27/327 |
| EP | 0 794 429 A1 | 9/1997 | ......... G01N/27/327 |
| EP | 0 849 589 A1 | 6/1998 | ......... G01N/27/327 |
| JP | 09-297121 A * | 11/1997 | ......... G01N/27/327 |
| JP | 2000-39416 | 2/2000 | ......... G01N/27/327 |

OTHER PUBLICATIONS

Pp. 92–93 of Principles of Biological Chemistry, David Page, Willard Grant Press, 1976.*
JPO computer translation of JP 09–297121 A (Yamamoto et al.).*

* cited by examiner

Primary Examiner—Alex Noguerola
(74) Attorney, Agent, or Firm—McDermott Will & Emery LLP (57) ABSTRACT

Disclosed is a highly responsive biosensor comprising a cholesterol-oxidizing enzyme and cholesterol esterase. The biosensor comprises: an electrically insulating base plate; an electrode system including a working electrode and a counter electrode formed on the base plate; a cover member joined with the base plate to define a sample supply pathway through which a sample solution is introduced from a sample supply port to the electrode system, the sample supply pathway being formed between the cover member and the base plate; and a reagent layer formed in the sample supply pathway, wherein the reagent layer contains a cholesterol-oxidizing enzyme, cholesterol esterase, an electron mediator, and a buffer having a buffering capacity in an acidic pH range.

18 Claims, 10 Drawing Sheets

BIOSENSOR AND METHOD OF SUBSTRATE QUANTIFICATION

BACKGROUND OF THE INVENTION

The present invention relates to a biosensor capable of rapid and simple quantification of a specific component contained in a sample and a method of substrate quantification.

Various biosensors have been proposed in order to readily quantify a specific component of a sample solution without diluting or stirring the sample solution. One example of such biosensors is proposed in the Japanese Laid-Open Patent Publication 2000-39416.

This biosensor is produced by forming an electrode system comprising a working electrode, a counter electrode and a reference electrode on an insulating base plate by screen printing or the like and subsequently forming an enzyme reaction layer comprising an oxidase and an electron mediator on the electrode system.

When a sample solution containing a substrate is dropped on the enzyme reaction layer of the biosensor, dissolution of the enzyme reaction layer takes place to cause a reaction between the enzyme and the substrate, which is accompanied by reduction of the electron mediator. Upon completion of the enzyme reaction, the reduced electron mediator is oxidized electrochemically, and the concentration of the substrate in the sample solution can be determined from the oxidation current value measured in this oxidizing step.

In order to determine the concentration of cholesterol in a sample solution such as blood, plasma or serum, this conventional biosensor includes two kinds of enzymes, that is, cholesterol esterase which hydrolyzes esterified cholesterol and cholesterol oxidase which oxidizes free cholesterol.

However, the measuring sample such as blood, plasma or serum has a pH buffering capacity around neutrality and therefore is not necessarily appropriate in terms of pH for the biosensor comprising cholesterol-oxidizing enzyme and cholesterol esterase.

In view of such problem, an object of the present invention is to provide a biosensor having high response characteristics and high performance by clarifying the appropriate pH and preferable buffers for the biosensor comprising cholesterol-oxidizing enzyme and cholesterol esterase.

BRIEF SUMMARY OF THE INVENTION

A biosensor in accordance with the present invention comprises: an electrically insulating base plate; an electrode system including a working electrode and a counter electrode formed on the base plate; a cover member joined with the base plate to define a sample supply pathway through which a sample solution is introduced from a sample supply port to the electrode system, the sample supply pathway being formed between the cover member and the base plate; and a reagent layer formed in the sample supply pathway, wherein the reagent layer contains a cholesterol-oxidizing enzyme, cholesterol esterase, an electron mediator, and a buffer having a buffering capacity in an acidic pH range.

A method of substrate quantification in accordance with the present invention is a method using a biosensor comprising: an electrically insulating base plate; an electrode system including a working electrode and a counter electrode formed on the base plate; a cover member joined with the base plate to define a sample supply pathway through which a sample solution is introduced from a sample supply port to the electrode system, the sample supply pathway being formed between the cover member and the base plate; and a reagent layer formed in the sample supply pathway, wherein the reagent layer contains a cholesterol-oxidizing enzyme, cholesterol esterase and an electron mediator, and this method comprises: a pretreatment step of mixing a buffer having a buffering capacity in an acidic pH range with the sample solution; a step of supplying the sample solution subjected to the pretreatment step to the biosensor; and a step of determining a substrate contained in the sample solution in the biosensor.

The present invention provides, in another aspect, a measuring system comprising: the above-described biosensor; voltage application means for applying a voltage between the working electrode and the counter electrode; and current detection means for detecting a current flowing between the working electrode and the counter electrode upon application of the voltage.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

A biosensor in accordance with the present invention comprises: an electrically insulating base plate; an electrode system including a working electrode and a counter electrode formed on the base plate; a cover member joined with the base plate to define a sample supply pathway through which a sample solution is introduced from a sample supply port to the electrode system, the sample supply pathway being formed between the cover member and the base plate; and a reagent layer formed in the sample supply pathway. This biosensor is characterized in that the reagent layer contains a cholesterol-oxidizing enzyme, cholesterol esterase, an electron mediator, and a buffer having a buffering capacity in an acidic pH range.

It is preferable to form a hydrophilic polymer layer on the electrode system.

Since the biosensor in accordance with the present invention contains the buffer having a buffering capacity in an acidic pH range in the reagent layer, the reagent layer is dissolved in a sample solution to make a reaction system acidic even when the sample solution is blood, plasma or serum having a buffering capacity around neutrality. Therefore, it is possible to improve the enzyme reactivity and thereby the response characteristics of the sensor. Also, even when the substrate concentration of the reaction system is high, it is possible to obtain satisfactory response values within a certain time, so that the measuring time can be reduced. Further, S/N ratio, i.e., measurement accuracy, is improved with the improvement in the response characteristics of the sensor. Also, the inclusion of the buffer in the reagent layer serves to smooth the reagent layer formed by application and drying of a solution. When a reagent layer is formed by drying an aqueous solution dissolving a reagent, the resultant reagent layer may become rough because the reagent crystallizes out into coarse crystals, and this phenomenon is evident especially when the reagent layer contains potassium ferricyanide as an electron mediator. When the reagent layer contains the buffer, however, the resultant layer becomes smooth. Without wishing to be bound by any particular theory, this is because the buffer crystallizes out into minute crystals when a solution dissolving the buffer is dried.

When the reagent layer is rough, a problem arises: when a sample solution is supplied to the sensor to dissolve the reagent layer, air may come in between the sample solution and the rough surface of the reagent layer, thereby to evolve air bubbles in the sample solution in which the reagent layer is dissolved. The evolution of the air bubbles may hinder the sample solution from moving smoothly in the sample supply pathway, making the quantification difficult. Therefore, the inclusion of the buffer in the reagent layer can eliminate this problem by smoothing the reagent layer. Further, the smooth reagent layer allows reduction in the volume or height of the sample supply pathway, realizing reduction in the amount of sample solution necessary for the quantification.

The buffer is preferably selected from the group consisting of succinic acid and its salts, D-tartaric acid, citric acid and its salts, phthalic acid and its salts, trans-actinic acid, formic acid, 3,3-dimethyl glutaric acid, sodium phenylacetate, acetic acid and its salts, sodium cacodylate, maleic acid and its salts, phosphoric acid and its salts, imidazole, 2,4,6-trimethyl pyridine, triethanolamine, tris (hydroxymethyl)aminomethane (hereinafter referred to as Tris), 2-morpholinoethanesulfonic acid (hereinafter referred to as MES), N-(2-acetamide)iminodiacetoacetic acid (hereinafter referred to as ADA), piperazine-N,N'-bis(2-ethane sulfonic acid)(hereinafter referred to as PIPES), N-2(acetamide)-2-aminoethanol sulfonic acid (hereinafter referred to as ACES), N,N-bis(2-hydroxyethyl)-2-aminoethane sulfonic acid (hereinafter referred to as BES), 3-morpholinopropanesulfonic acid (hereinafter referred to as MOPS), N-tris(hydroxymethyl)methyl-2-aminoethane sulfonic acid (hereinafter referred to as TES), N-2-hydroxyethyl piperazine-N'-2-ethane sulfonic acid (hereinafter referred to as HEPES), and chloroacetic acid.

In view of high dissolution, preferable among them are succinates such as potassium succinate and sodium succinate, phosphates such as dipotassium hydrogenphosphate, potassium dihydrogenphosphate, disodium hydrogenphosphate and sodium dihydrogenphosphate, acetates such as potassium acetate and sodium acetate, phthalates such as potassium hydrogenphthalate, sodium phthalate and potassium phthalate, and maleates such as sodium hydrogenmaleate, potassium maleate and sodium maleate. The use of the succinic acid or its salts, phophoric acid or its salts, maleic acid or its salts, phthalic acid or its salts yields a biosensor with remarkably improved response values and excellent response linearity. In view of storage characteristics of the biosensor, succinic acid is more preferable.

Since the above-listed buffers are soluble in water, a layer including the buffer is promptly dissolved in a sample solution upon introduction of the sample solution, thereby facilitating the enzyme reaction and electrode reaction.

The buffer may be adjusted, if necessary, so as to have a buffering capacity in a predetermined pH range by an acid such as hydrochloric acid or acetic acid, or an alkali such as NaOH or KOH before being supplied into the sample supply pathway of the biosensor.

In order to improve the response linearity and obtain satisfactory response values within a certain time, the pH is preferably 4 to 6.5, and more preferably 4 to 5.5.

Since the measuring sample may have a buffering capacity, two or more kinds of buffers may be added to the biosensor. Preferable combinations of the buffers include a mixture of succinic acid and maleic acid, a mixture of succinic acid and phosphoric acid, and a mixture of maleic acid and Tris.

The amount of the buffer is preferably 5 to 1000 nmol per sensor of disposable type designed for measuring a sample solution of 0.04 to 20 $\mu$l blood in view of the effective smoothing of the reagent layer containing the buffer as well as the reduction of blank response. More preferably, it is 20 to 500 nmol per sensor in view of the improvement of dissolution of the reagent layer containing the buffer as well as the reduction of the blank value. Herein, blank response refers to the value of a current flowing in response to a measuring sample having a zero substrate concentration such as water and is hereinafter referred to as blank value. As for the amount of the enzyme required for reducing the measuring time by about 4 minutes to facilitate the quantification, the preferable amount of cholesterol esterase is 0.1 to 10 U per sensor and that of cholesterol oxidase is 0.03 to 3 U. Herein, the measuring time refers to a period of time necessary from the introduction of a sample to the sensor until obtaining a response value.

In a preferable mode of the present invention, the cholesterol-oxidizing enzyme and cholesterol esterase are carried separately from the electron mediator. According to this mode, it is possible to obtain a biosensor in which the blank value is low. Further, since an increase of the response value due to storage is prevented from occurring, it is possible to obtain a biosensor having excellent storage characteristics.

In another preferable mode of the present invention, the buffer is carried while being mixed with the cholesterol-oxidizing enzyme or cholesterol esterase. According to this mode, the layer containing the cholesterol-oxidizing enzyme or cholesterol esterase can be smoothed, so that evolution of air bubbles can be prevented upon introduction of the measuring sample to the sensor.

In still another preferable mode of the present invention, the buffer is carried while being mixed with the electron mediator. According to this mode, the layer containing the electron mediator can be smoothed, so that evolution of air bubbles can be prevented upon introduction of the measuring sample.

In a preferable mode of the present invention, the buffer is carried separately from the cholesterol-oxidizing enzyme, the cholesterol esterase and the electron mediator in the sample supply pathway and the buffer is carried at a position closer to the sample supply port than the cholesterol-oxidizing enzyme, the cholesterol esterase and the electron mediator. According to this mode, the measuring sample dissolves the buffer right after the introduction of the measuring sample into the biosensor, thereby producing the effect of promptly adjusting the pH of the measuring sample on the acidic side.

In another preferable mode of the present invention, the biosensor further comprises a filter in the sample supply pathway. The filter filters blood hemocytes when the measuring sample is blood, thereby eliminating the influence of the blood hemocytes on the electrodes. When the filter is disposed at a part of the sample supply pathway close to the sample supply port, the blood hemocytes can be effectively removed from the measuring sample, so it is preferable to dispose the filter close to the sample supply port.

When the filter is set close to the sample supply port in the sample supply pathway, the blood hemocytes are effectively prevented from coming in contact with the reagents such as enzymes and electron mediator and the electrodes when the measuring sample is blood.

As the filter, glass filter, filter paper, cellulose fibers or the like may be used.

The biosensor of the present invention is designed to measure body fluids. Examples of the body fluids include blood, plasma, serum, lymph, interstitial fluid and sweat. Particularly, part of cholesterol contained in blood, plasma and serum exists as cholesterol ester combined with a fatty acid. In the biosensor of the present invention, which contains cholesterol esterase, cholesterol ester is converted to free cholesterol by the catalytic action of cholesterol esterase, and the converted cholesterol is oxidized by cholesterol oxidase or the like.

The present invention provides, in another aspect, a measuring system comprising: the above-described biosensor; voltage application means for applying a voltage between the working electrode and the counter electrode; and current detection means for detecting a current flowing between the working electrode and the counter electrode upon application of the voltage.

The measuring system in accordance with the present invention preferably includes a display unit for displaying a current detected by the current detection means or a converted value of the current.

The present invention further provides a method of substrate quantification using a biosensor comprising: an electrically insulating base plate; an electrode system including a working electrode and a counter electrode formed on the base plate; a cover member joined with the base plate to define a sample supply pathway through which a sample solution is introduced from a sample supply port to the electrode system, the sample supply pathway being formed between the cover member and the base plate; and a reagent layer formed in the sample supply pathway, wherein the reagent layer contains a cholesterol-oxidizing enzyme, cholesterol esterase and an electron mediator, the method comprising: a pretreatment step of mixing a buffer having a buffering capacity in an acidic pH range with the sample solution; a step of supplying the sample solution subjected to the pretreatment step to the biosensor; and a step of determining a substrate contained in the sample solution in the biosensor.

According to this method, the pretreatment step causes the pH of the measuring sample to be adjusted on the acidic side, thereby improving reactivity of the enzymes and response characteristics of the sensor.

The present invention provides an enzyme reagent comprising a buffer having a buffering capacity in an acidic pH range and enzymes, wherein the enzymes are at least a cholesterol-oxidizing enzyme and cholesterol esterase. A simple addition of this enzyme reagent to the biosensor yields a biosensor with improved response characteristics.

Examples of the cholesterol-oxidizing enzyme include cholesterol oxidase and cholesterol dehydrogenase.

Examples of the electron mediator include potassium ferricyanide, p-benzoquinone and its derivatives, phenazine methosulfate, methylene blue, and ferrocene and its derivatives. Among them, potassium ferricyanide is preferable since stable oxidation/reduction is possible in the air.

The hydrophilic polymer can prevent the separation of the reagent layer containing reagents such as cholesterol-oxidizing enzyme, cholesterol esterase, electron mediator and buffer from the surface of the electrode system or base plate. The hydrophilic polymer further has the effect of preventing cracking of the surface of the reagent layer. Thus, it is effective for improving the reliability of the biosensor. Examples of such hydrophilic polymer include carboxymethyl cellulose, hydroxyethyl cellulose, hydroxypropylcellulose, methyl cellulose, ethyl cellulose, ethyl hydroxyethyl cellulose, carboxymethyl ethyl cellulose, polyvinyl pyrrolidone, polyvinyl alcohol, polyamino acid such as polylysine, polystyrene sulfonic acid, gelatin and its derivatives, a polymer of acrylic acid or its salts, a polymer of methacrylic acid or its salts, starch and its derivatives, a polymer of maleic anhydride or its salts, and agarose gel and its derivatives. Particularly preferable are carboxymethyl cellulose, hydroxyethyl cellulose and polyvinyl pyrrolidone, since they have sufficient viscosity.

The present invention also aims to provide a biosensor capable of highly accurate quantification with only a small amount of sample. This aim is suitably achieved by a sensor having a following structure: the dimensions of the sample supply pathway extending from the sample supply port to the air vent are preferably 0.4 to 4 mm in width, 0.05 to 0.5 mm in height, and 2 to 10 mm in length. In a more preferable sensor, the dimensions of the sample supply pathway are 0.5 to 2 mm in width, 0.05 to 0.2 mm in height, and 3 to 5 mm in length, and the amount of sample is 0.075 to 2 $\mu$l.

In the following, the present invention will be further described with reference to examples. Such examples, however, are not to be construed as limiting in any way the scope of the present invention.

EXAMPLE 1

Figure 1:
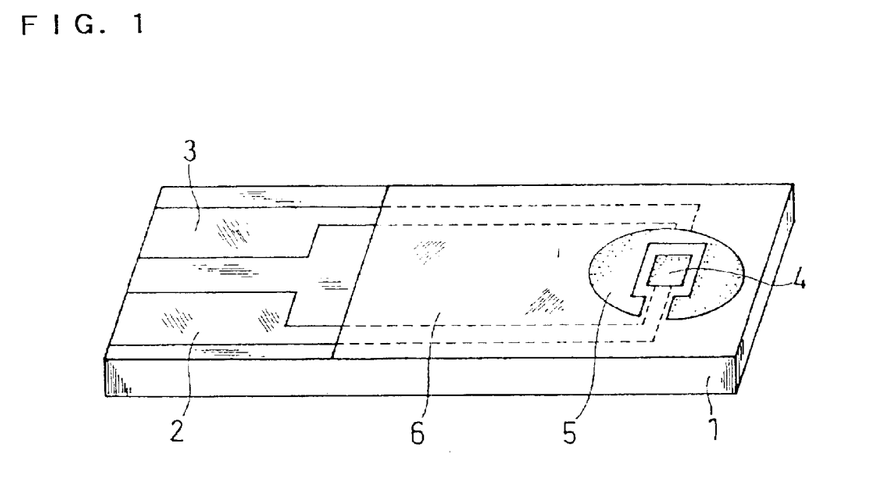
FIG. 1 is a perspective view of a biosensor used for demonstrating the effect of the use of a buffer in a biosensor in accordance with the present invention.

FIG. 1 is a perspective view of a biosensor used for demonstrating the effect of the use of a buffer having a buffering capacity in an acidic pH range in a biosensor in accordance with the present invention. A silver paste is printed on an electrically insulating base plate 1 made of polyethylene terephthalate by screen printing to form leads 2 and 3. Then, a conductive carbon paste containing a resin binder is printed on the base plate 1 to form a working electrode 4. The working electrode 4 is in contact with the lead 2. Further, an insulating paste is printed on the base plate 1 to form an insulating layer 6. The insulating layer 6 covers the outer periphery of the working electrode 4 so as to keep the exposed area of the working electrode 4 constant. Thereafter, a conductive carbon paste containing a resin binder is printed on the base plate 1 so as to be in contact with the lead 3, thereby to form a ring-shaped counter electrode 5. The working electrode 4 and counter electrode 5 constitute an electrode system.

By using the above-described biosensor, the following experiments on determination of cholesterol concentration were conducted in order to clarify the appropriate pH and preferable buffers for the biosensor comprising a cholesterol-oxidizing enzyme and cholesterol esterase.

First, an aqueous solution containing cholesterol esterase, cholesterol oxidase and one kind of buffer was prepared. Then, an aqueous solution containing potassium ferricyanide and Triton X-100 was prepared. As a measuring sample, human serum was used. In order to obtain a current value in response to 0 mg/ml cholesterol concentration, water was used in place of human serum. The buffer was selected from succinic acid, maleic acid, phosphoric acid and Tris.

These three kinds of solutions were stirred and mixed with each other in a tube. The concentrations of respective reagents and cholesterol in the resultant mixed solution were as follows:

Cholesterol esterase: 200 unit (U)/ml
Cholesterol oxidase: 1000 U/ml
Buffer: 100 mM
Potassium ferricyanide: 300 mM
Triton X-100: 2 wt %
Cholesterol: 0 to 116 mg/dl In the mixed solution, esterified cholesterol contained in the serum was hydrolyzed by cholesterol esterase. The cholesterol which was produced by the hydrolysis and cholesterol contained originally in the serum were oxidized by cholesterol oxidase, while potassium ferricyanide was reduced to potassium ferrocyanide in the solution.

Next, the mixed solution of 10 μl (microliter) was dropped onto the electrode system as shown in FIG. 1. Twenty seconds after the mixing of the three kinds of solutions, a voltage of 500 mV was applied to the working electrode using the counter electrode as reference. At this time, the ferrocyanide ions contained in the mixed solution were oxidized, whereby a current flowed between the working electrode and counter electrode. The value of this current was measured 5 seconds after the application of the voltage. Lastly, the pH of the mixed solution was measured since the serum has pH buffering capacity.

Figure 2:
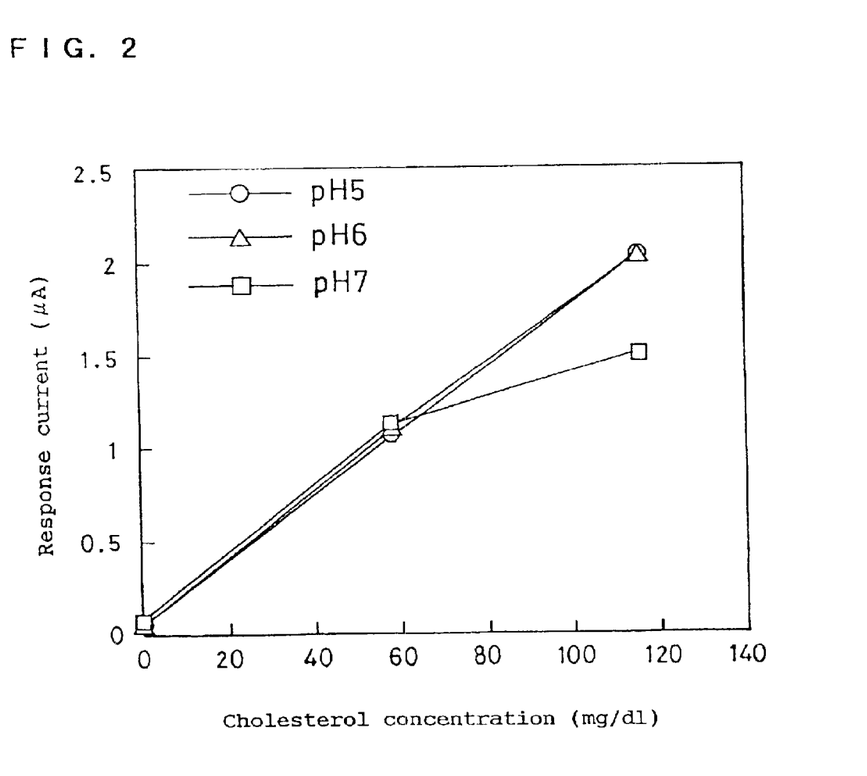
FIG. 2 is a graph showing the response characteristics of the biosensor comprising a maleic acid as a buffer.

In this manner, by using maleic acid as an example of the buffer, mixed solutions of various total cholesterol concentrations were prepared, and the current values in response to these solutions were measured. The response current value (ordinate) was plotted against the total cholesterol concentration of the mixed solutions (abscissa) in FIG. 2 in order to show the response characteristics of the sensor. When the pH of the solution was in an acidic range, the response value was high and better response linearity was obtained. Also, since it is possible in an acidic pH range to obtain response linearity within a certain time, the addition of the buffer having a buffering capacity in an acidic pH range enabled reduction of measuring time.

Figure 3:
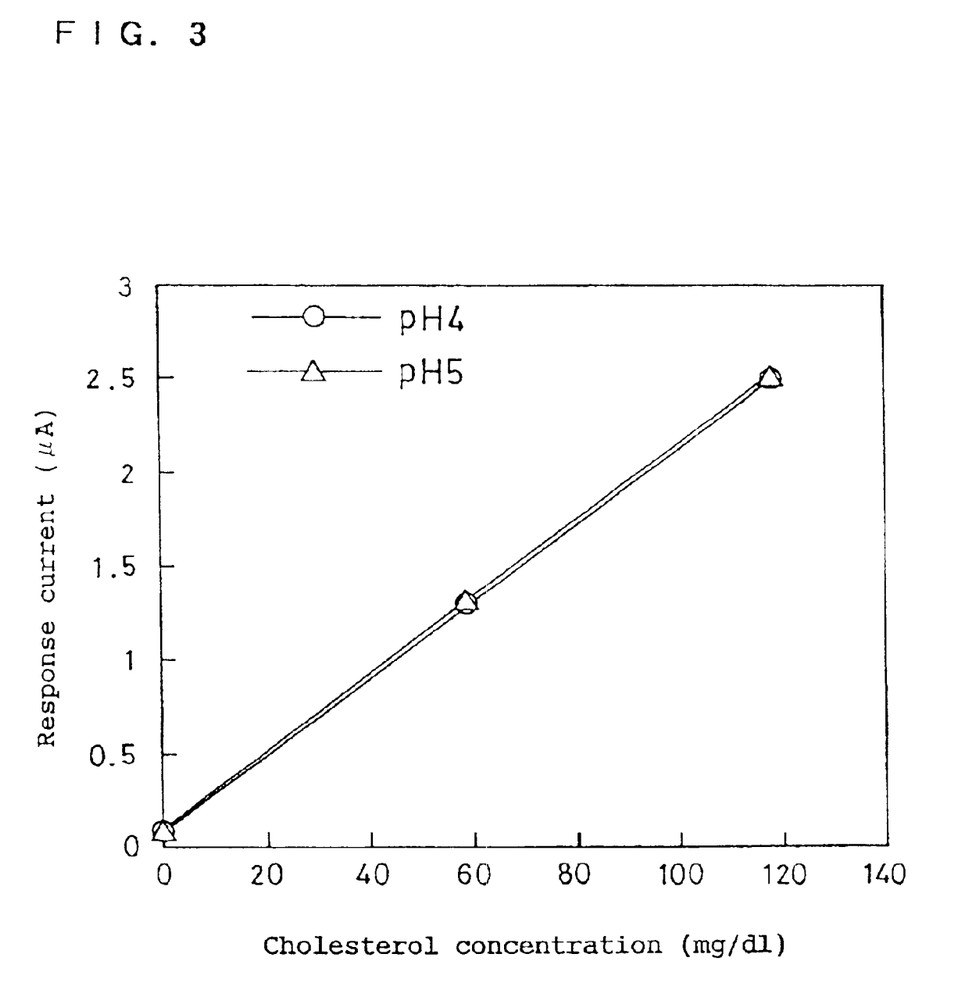
FIG. 3 is a graph showing the response characteristics of the biosensor comprising a succinic acid as a buffer.

Next, the response characteristics of the sensor comprising succinic acid as the buffer are shown in FIG. 3. In both cases of pH 4 and pH 5, the response value was high and better response linearity was obtained. Further, the improvement of response linearity makes it possible to improve S/N ratio, that is, measurement accuracy.

Figure 4:
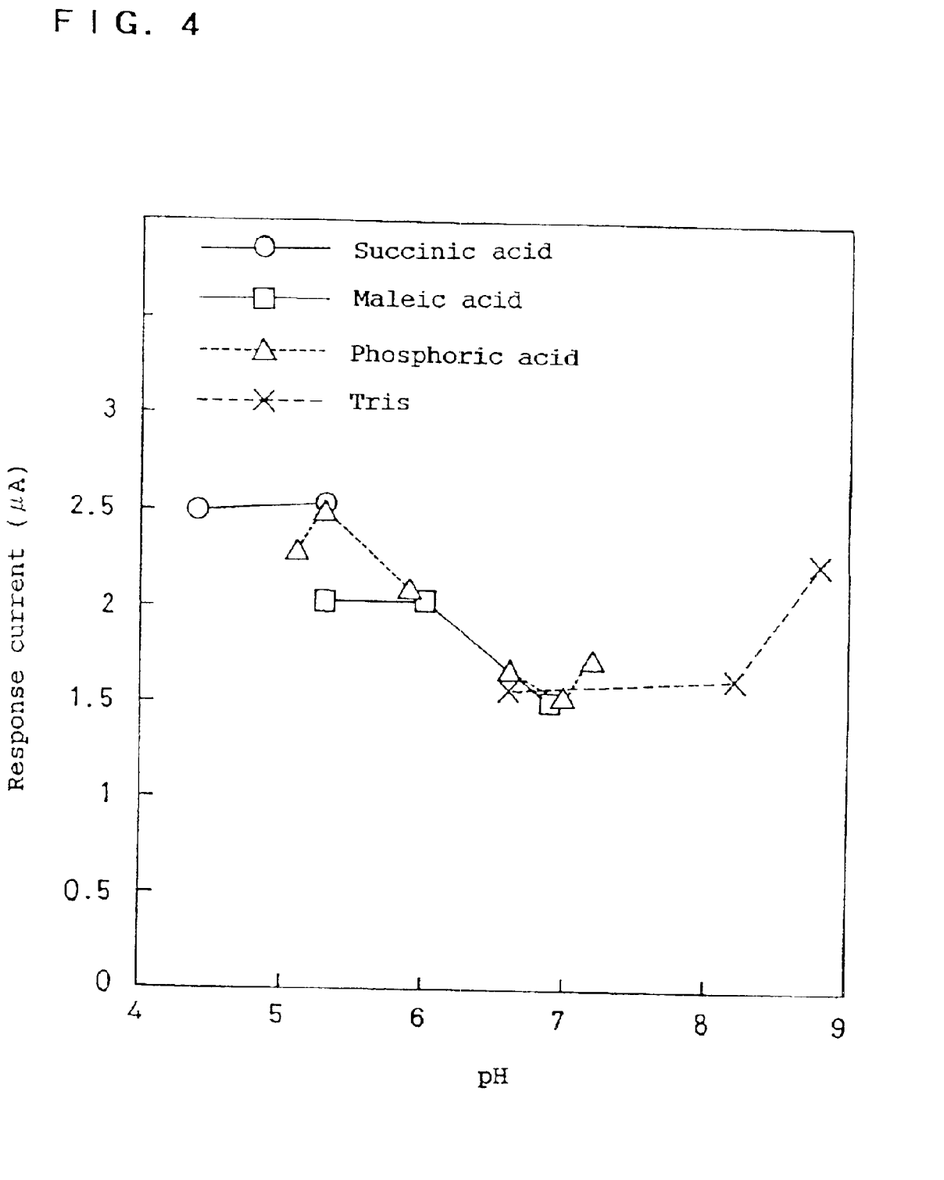
FIG. 4 is a graph illustrating the response characteristics of the biosensors comprising various buffers.

The results of the use of succinic acid, maleic acid, phosphoric acid or Tris as the buffer are shown in FIG. 4. It is clear from FIG. 4 that the sensor response is dependent on the pH. When the pH of the mixed solution was adjusted in an acidic range, the response value was higher. When the pH of the mixed solution was higher than 8, however, the blank response (the current value in response to 0 mg/dl of cholesterol) became high, indicating that such pH is inappropriate. The preferable pH was 4 to 6.5, and 4 to 5.5 was more preferable.

As regards the optimal pH for the enzymes used in the experiments, it was 6.5 or lower for cholesterol esterase and about 7 for cholesterol oxidase. Thus, these results indicate that when the pH of the sample solution is adjusted to a pH close to the optimal pH for cholesterol esterase, the response value becomes higher.

EXAMPLE 2

Figure 5:
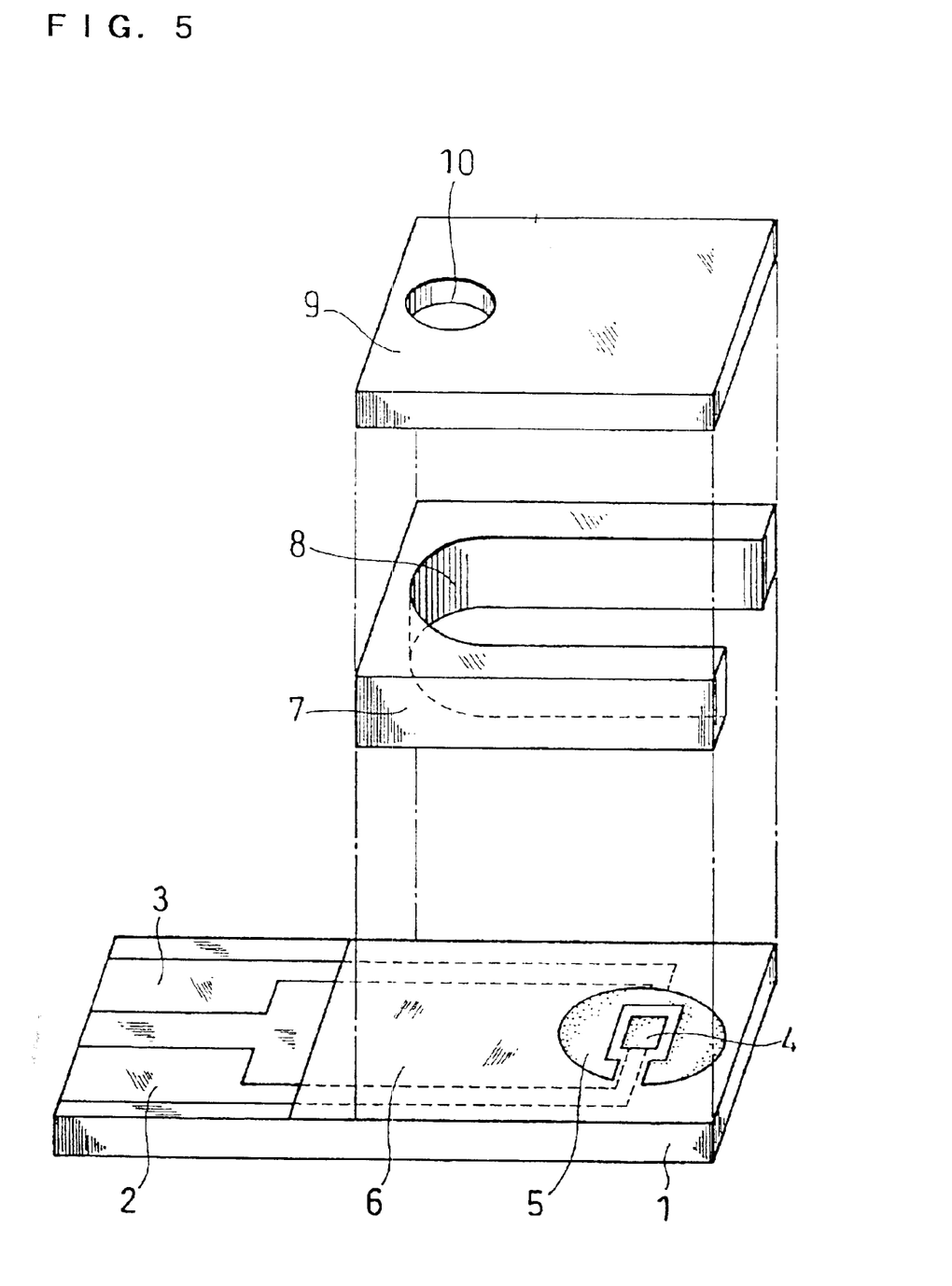
FIG. 5 is an exploded perspective view of a biosensor in an example of the present invention from which the reagent layer is omitted.
Figure 6:
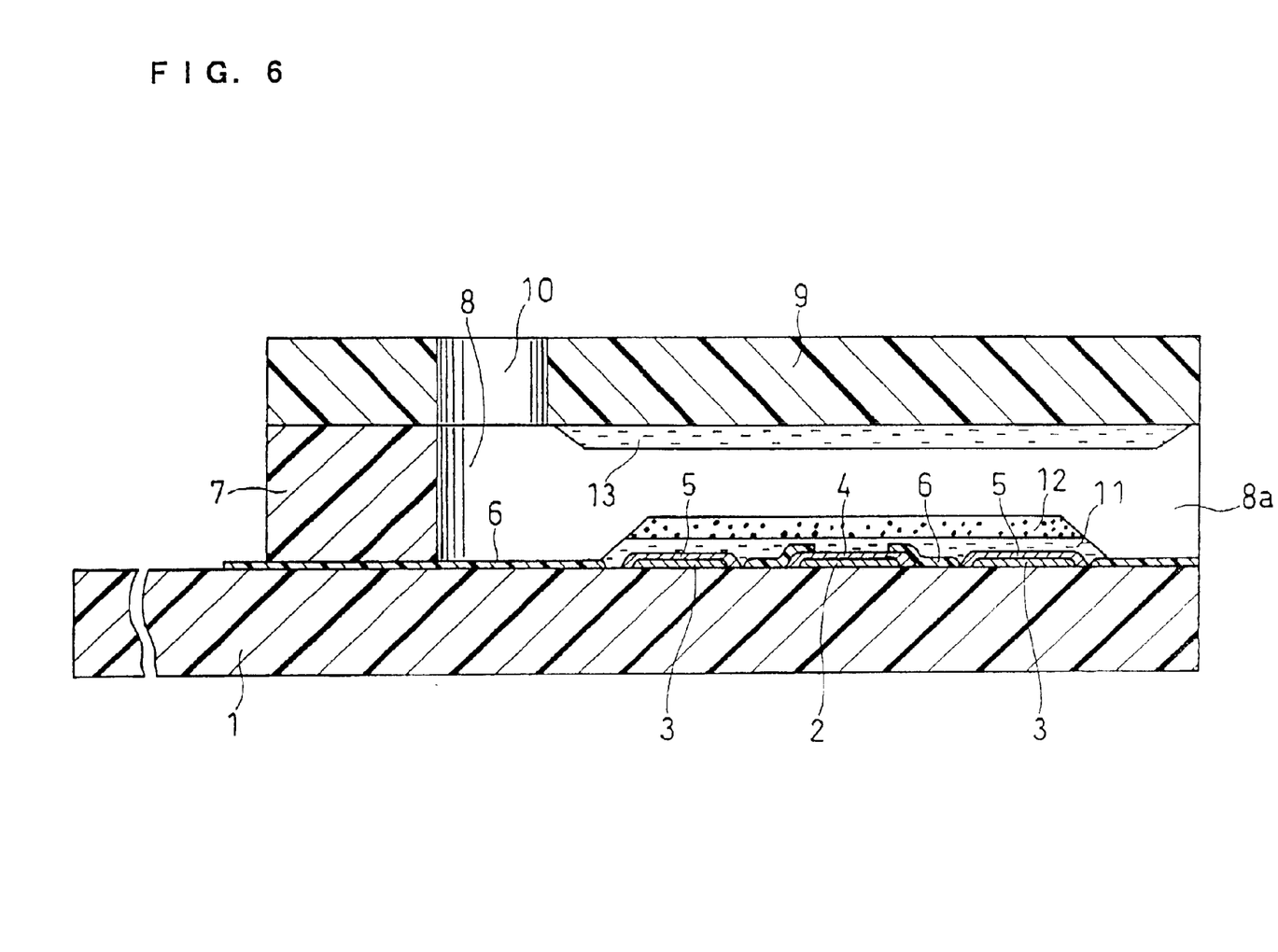
FIG. 6 is a longitudinal cross-sectional view of the biosensor.

This example will be explained with reference to FIGS. 5 and 6. FIG. 5 is an exploded perspective view of a biosensor of this example from which the reagent layers are omitted, and FIG. 6 is a longitudinal cross-sectional view of the biosensor. A base plate 1 has the same electrode system as shown in FIG. 1. A cover member to be joined with the base plate is composed of a spacer 7 having a slit 8 and a cover 9 having an air vent 10. After reagent layers are formed in a manner as described later, the spacer 7 and the cover 9 are bonded to the base plate 1 in a positional relationship as shown by the dashed lines in FIG. 5 to fabricate the biosensor. The biosensor has a sample supply pathway formed in the slit 8 of the spacer 7. An open end 8a of the slit 8, which is at one end of the sensor, serves as a sample supply port of the sample supply pathway. The base plate 1 used in this example is 6 mm in width and 30 mm in length. The internal dimensions of the sample supply pathway extending from the sample supply port to the air vent are 2.0 mm in width, 0.1 mm in height, and 5.0 mm in length.

A 0.5 wt % aqueous solution of carboxymethyl cellulose (which is a kind of hydrophilic polymer and is hereinafter referred to as CMC) was dropped in an amount of 4 μl over the base plate 1 with the electrode system formed thereon and dried at 50° C. for 15 minutes to form a CMC layer 11. Then, over the CMC layer 11 was formed an electron mediator-buffer layer 12 containing succinic acid as the buffer and potassium ferricyanide as the electron mediator. The electron mediator-buffer layer 12 was formed as follows: First, potassium ferricyanide was added to and dissolved in a 20 mM buffer solution of succinic acid prepared to pH 5 such that the concentration of potassium ferricyanide in the resultant solution became 75 mM. This succinic acid buffer solution containing potassium ferricyanide was then dropped in an amount of 4 μl over the CMC layer 11 and dried at 50° C. for 15 minutes.

Meanwhile, the cover member was fabricated by laminating the spacer 7 and cover 9 to form the sample supply pathway in the slit 8. An aqueous solution containing 900 U/ml cholesterol esterase, 400 U/ml cholesterol oxidase, and 1.6 wt % Triton X-100 and 30 mM sodium cholate as surfactants was dropped in an amount of 0.5 μl onto one face of the cover 9 facing the slit 8. Thereafter, this solution was freeze-dried to form an enzyme-surfactant layer 13. The cover member with the enzyme-surfactant layer 13 formed thereon was bonded to the base plate 1 with the CMC layer 11 and electron mediator-buffer layer 12 formed thereon, which gave the biosensor.

When a measuring sample was introduced into the sensor, the succinic acid contained in the electron mediator-buffer layer 12 was dissolved, adjusting the pH of the solution in the sensor on the acidic side. Thus, the activity of the enzymes was improved to produce the effect of improving the response characteristics of the sensor. Further, it was possible to obtain satisfactory response within a certain time, thereby producing the effect of shortening the measuring time. Also, the succinic acid contained in the electron mediator-buffer layer 12 smoothed the layer 12 itself, producing the effect of preventing evolution of air bubbles on the electrode system. Further, since the enzymes were carried separately from the electron mediator, the blank value was low in the biosensor of this example. Since the enzymes were carried separately from the electron mediator, the biosensor had excellent storage characteristics: after the biosensor was stored, the response value was equivalent to that of the biosensor immediately after its production, and an increase in the response value after storage due to increased blank value, etc., was therefore suppressed.

The enzymes or potassium ferricyanide may be disposed at various locations in the biosensor unless the effects of the present invention are impaired. For example, the potassium ferricyanide may be disposed at a part of the sample supply pathway which is not on the CMC layer.

Although this example used Triton X-100 and sodium cholate as the surfactants, it is also possible to use other surfactants such as octyl thioglucoside, Lubrol, cholic acid, sodium deoxycholate, digitonin, dodecyl-maltoside, sucrose monolaurate, sodium taurodeoxycholate, and polyoxyethylene-pt-octyl phenyl ether.

As for the method of measuring the oxidation current of the electron mediator reduced in connection with the enzyme reaction, both of the two-electrode system consisting only of the working electrode and counter electrode and the three-electrode system including an additional reference electrode are possible.

EXAMPLE 3

Figure 7:
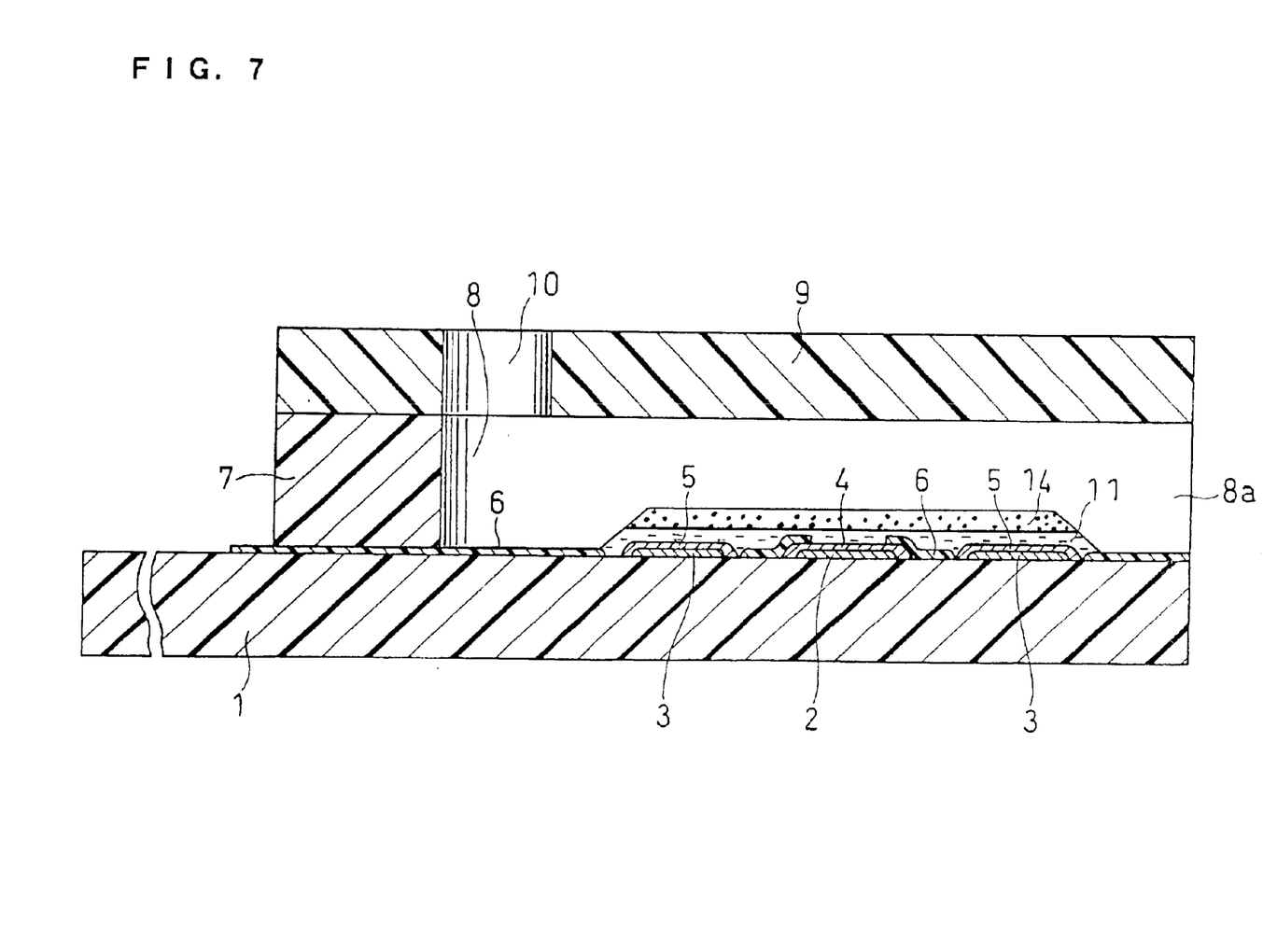
FIG. 7 is a longitudinal cross-sectional view of a biosensor in another example of the present invention.

A biosensor of this example is shown in FIG. 7. First, the CMC layer 11 was formed on the base plate 1 in the same manner as in EXAMPLE 2. Next, an aqueous solution was prepared by adding cholesterol esterase, cholesterol oxidase, potassium ferricyanide, Triton X-100 and sodium cholate to a buffer solution of maleic acid adjusted to pH 5. The concentrations of respective reagents in the aqueous solution were as follows: 200 mM maleic acid; 900 U/ml cholesterol esterase; 400 U/ml cholesterol oxidase; 600 mM potassium ferricyanide; 1.6 wt % Triton X-100; and 30 mM sodium cholate. The aqueous solution was dropped in an amount of 0.5 µl over the CMC layer 11 and freeze-dried to form an enzyme-surfactant-electron mediator-buffer layer 14.

In this example, all the reagents except CMC were dropped and dried at one time as in the above manner. Thus, this example has an advantage that the production of the sensor is the simplest. Also, when a measuring sample was introduced into the sensor, the maleic acid contained in the enzyme-surfactant-electron mediator-buffer layer 14 was dissolved, adjusting the pH of the solution in the sensor on the acidic side. Thus, the activity of the enzymes was improved to produce the effect of improving the response characteristics of the sensor.

EXAMPLE 4

Figure 8:
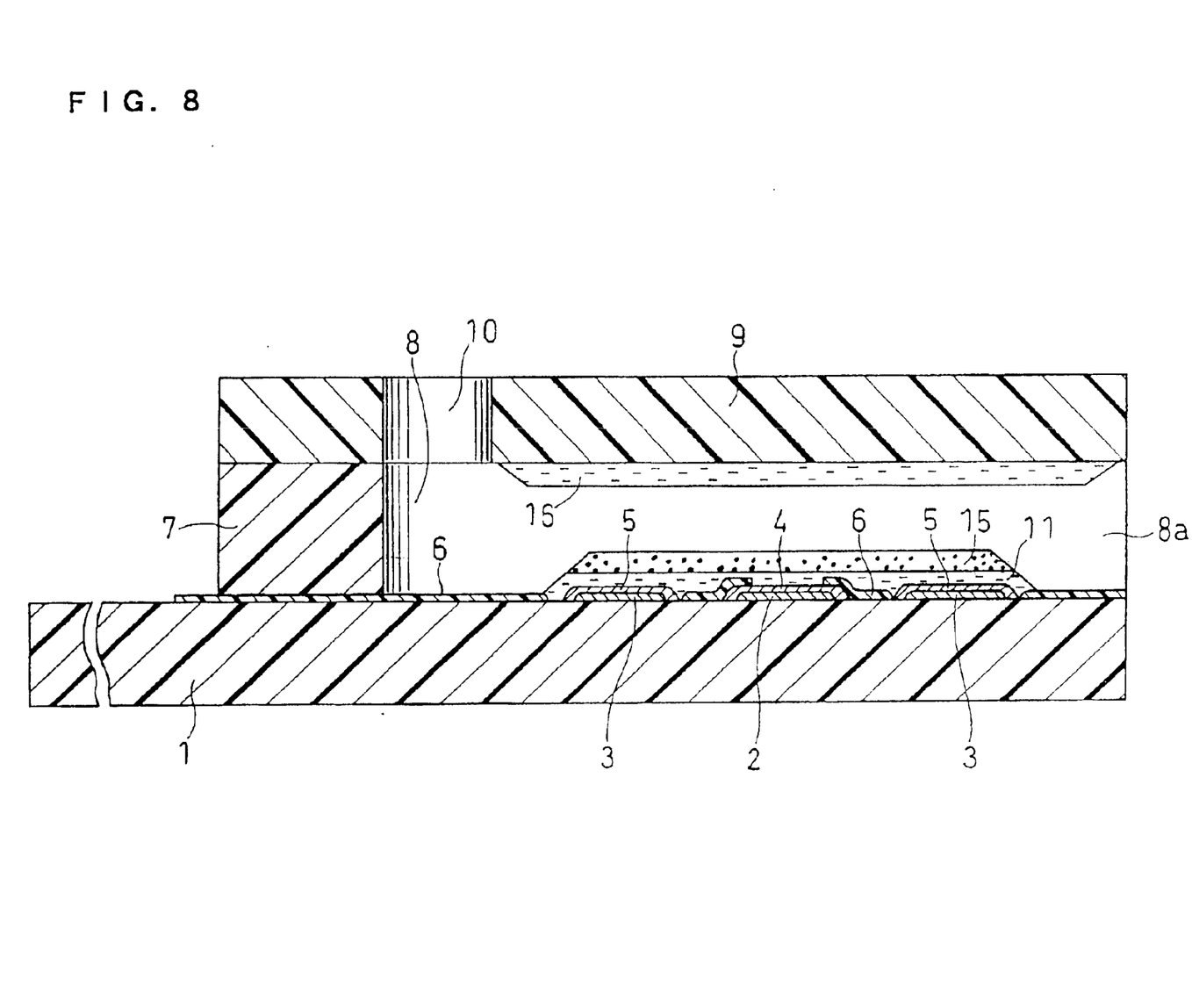
FIG. 8 is a longitudinal cross-sectional view of a biosensor in still another example of the present invention.

A biosensor of this example is shown in FIG. 8. First, the CMC layer 11 was formed on the base plate 1 with the electrode system formed thereon in the same manner as in EXAMPLE 2. Next, an aqueous solution containing 0.16 wt % Triton X-100, 3 mM sodium cholate, and 75 mM potassium ferricyanide was dropped in an amount of 5 µl over the CMC layer 11 and dried at 50° C. for 15 minutes to form a surfactant-electron mediator layer 15.

Separately, an aqueous solution containing 900 U/ml cholesterol esterase, 400 U/ml cholesterol oxidase, and 20 mM phosphoric acid as the buffer was dropped in an amount of 0.5 µl on one face of the cover 9 facing the sample supply pathway. Thereafter, the aqueous solution was freeze-dried to form an enzyme-buffer layer 16.

When a measuring sample was introduced into the sensor, the phosphoric acid contained in the enzyme-buffer layer 16 was dissolved, adjusting the pH of the solution in the sensor on the acidic side. Thus, the activity of the enzymes was improved to produce the effect of improving the response characteristics of the sensor. Also, the phosphoric acid contained in the enzyme-buffer layer 16 smoothed the layer 16 itself, producing the effect of preventing evolution of air bubbles on the electrode system. Further, since the enzymes were carried separately from the electron mediator, the biosensor of this example had excellent storage characteristics wherein the blank value was low and the increase of the response value due to storage was prevented.

EXAMPLE 5

Figure 9:
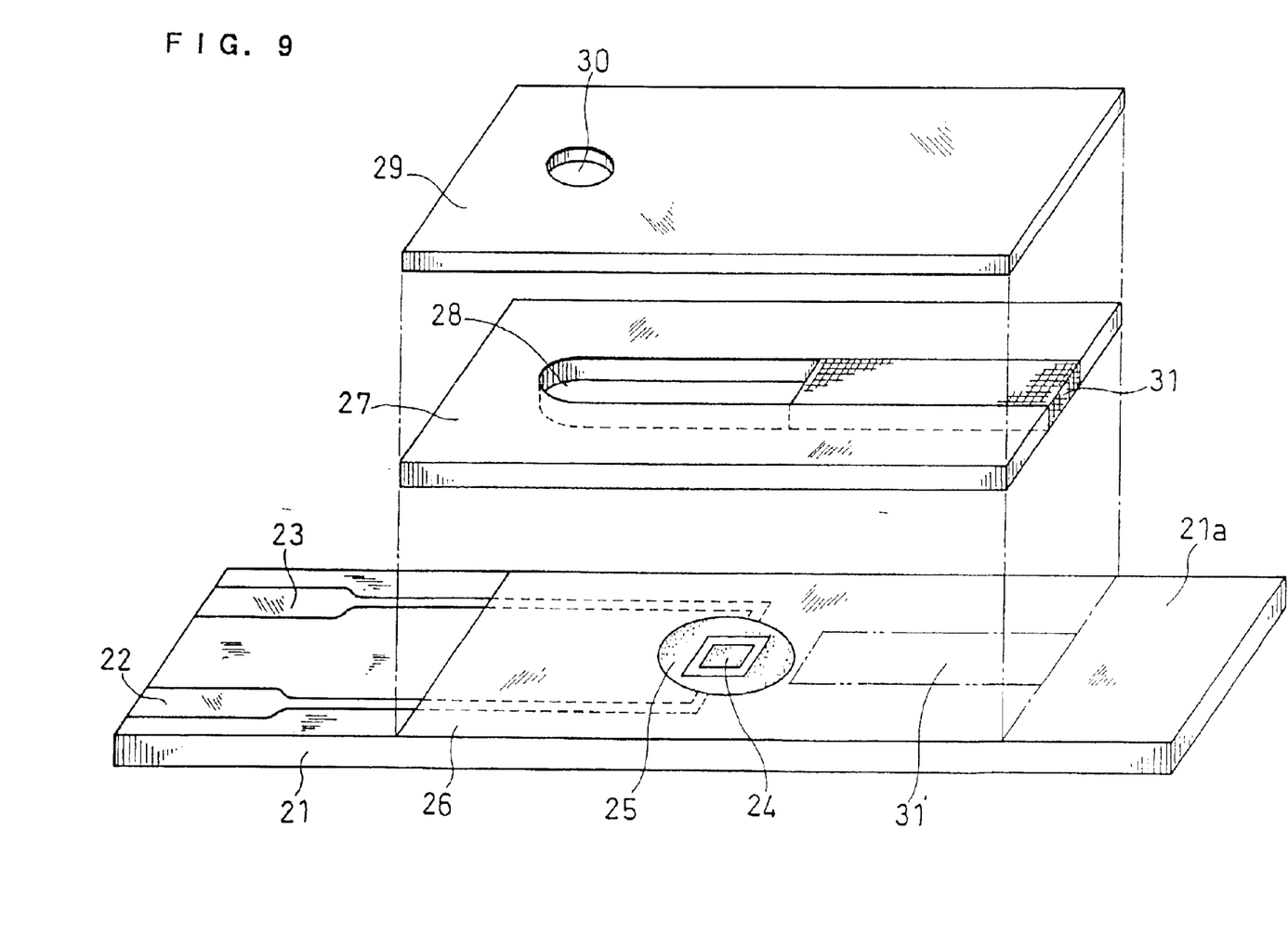
FIG. 9 is an exploded perspective view of a biosensor in still another example of the present invention from which the reagent layer is omitted.
Figure 10:
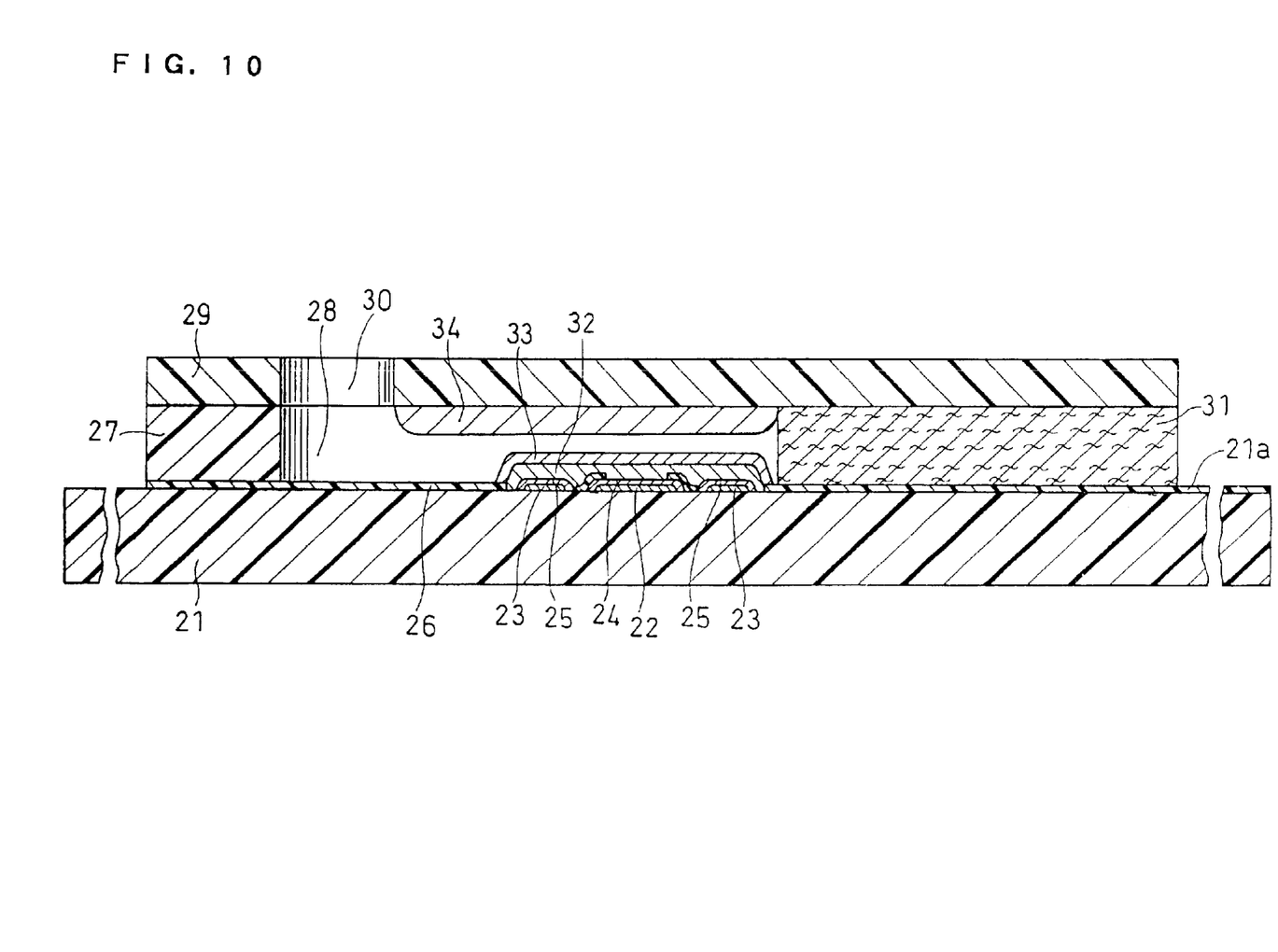
FIG. 10 is a longitudinal cross-sectional view of the biosensor.

This example will be explained with reference to FIGS. 9 and 10. FIG. 9 is an exploded perspective view of a biosensor of this example from which the reagent layers are omitted, and FIG. 10 is a longitudinal cross-sectional view of the biosensor.

In the same manner as in EXAMPLE 1, a base plate 21 has a working electrode 24 connected to a lead 22, a counter electrode 25 connected to a lead 23, and an insulating layer 26. A CMC layer 32 was formed on the base plate 21 so as to cover the electrode system in the same manner as in EXAMPLE 2. A 75 mM aqueous solution of potassium ferricyanide was dropped in an amount of 5 µl over the CMC layer 32, and the aqueous solution was dried at 50° C. for 15 minutes to form an electron mediator layer 33.

Meanwhile, the cover member was fabricated by laminating a spacer 27 and a cover 29. An aqueous solution containing 900 U/ml cholesterol esterase, 400 U/ml cholesterol oxidase, and 1.6 wt % Triton X-100 and 30 mM sodium cholate as surfactants was dropped in an amount of 0.5 µl onto one face of the cover 9 facing the sample supply pathway. Thereafter, this solution was freeze-dried to form an enzyme-surfactant layer 34. Further, a filter 31 for filtering solid components of a measuring sample was disposed upstream of the enzyme-surfactant layer 34 in the sample supply pathway.

The filter 31 has, when the measuring sample is blood, for example, the function of filtering blood hemocytes and thereby eliminating the influence of the blood hemocytes on the electrodes. As shown in FIG. 10, when the filter 31 is disposed at a part of the sample supply pathway close to the sample supply port, the blood hemocytes can be effectively removed from the measuring sample, so it is preferable to dispose the filter 31 close to the sample supply port. When the filter 31 is set close to the sample supply port in the sample supply pathway, the blood hemocytes are effectively prevented from coming in contact with the electron mediator layer 33, enzyme-surfactant layer 34 and electrodes when the measuring sample is blood. The filter is composed of a porous material having three-dimensional communicating spaces such as glass filter, paper filter or cellulose fibers. This porous material allows blood to move toward the electrode system by capillary action while having the function of filtering the blood hemocytes by the difference in flow resistance between the plasma and the blood hemocytes.

When the base plate 21, spacer 27, and cover 29 were laminated in a positional relationship as shown in dashed lines of FIG. 9, the filter 31 came in contact with the surface of the base plate 21 at a portion represented by numeral 31'. A sensor end 21a of the base plate 21 served as the sample supply port of the sample supply pathway. A sample supplied to the sample supply port was absorbed by the filter 31 and moved through the filter 31 to the electrode system by capillary action. Succinic acid, which is a buffer, was carried within the filter 31 disposed upstream of the enzyme-surfactant layer 34 and electron mediator layer 33 in the following manner: the filter 31 was disposed at a predetermined part of the sensor, after which an aqueous solution of succinic acid was dropped onto the filter 31 and freeze-dried.

In this example, since succinic acid was situated upstream of the enzymes and potassium ferricyanide in the sample supply pathway, the measuring sample dissolved succinic acid right after its introduction into the sensor, so that the pH of the measuring sample was adjusted on the acidic side promptly. Thus, the activity of the enzymes was improved in the biosensor, producing the effect of improving the response characteristics of the sensor.

EXAMPLE 6

Figure 11:
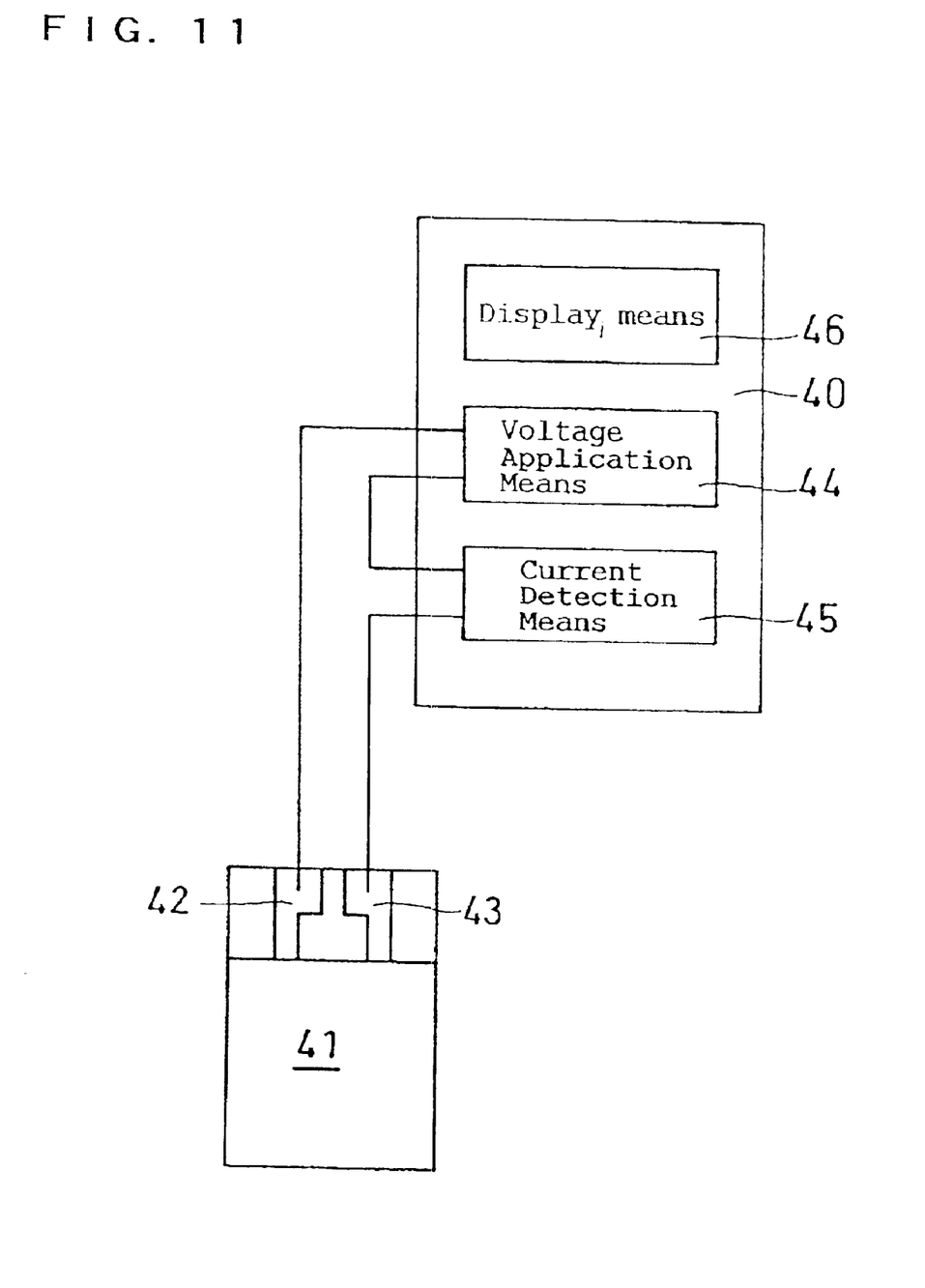
FIG. 11 is a block diagram illustrating the circuit configuration of a measuring system in an example of the present invention.

FIG. 11 is a block diagram illustrating the circuit configuration of a measuring system in an example of the present invention. A measurement device 40 comprises a voltage application unit 44 for applying a controlled voltage between the working electrode and counter electrode through a working electrode lead 42 and a counter electrode lead 43 of a biosensor 41 and a current detection unit 45 for detecting a current flowing between the working electrode and counter electrode of the sensor. The detected current value is displayed by a display unit 46. The display unit 46 can display the detected current value, for example, as the cholesterol value by making conversions of the detected current value.

As described above, the present invention can provide a biosensor with improved response values and response linearity by adding a buffer to a reaction system of the biosensor and thereby adjusting the pH of the reaction system in an acidic pH range. Also, since it is possible to obtain satisfactory response values within a certain time, the present invention can realize the reduction of the measuring time. Further, since the inclusion of the buffer in a reagent layer serves to smooth the reagent layer, the present invention can prevent evolution of air bubbles upon introduction of a measuring sample to the biosensor.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising: an electrically insulating base plate; an electrode system including a working electrode and a counter electrode formed on said base plate; a cover member joined with said base plate to define a sample supply pathway through which a sample solution is introduced from a sample supply port to said electrode system, said sample supply pathway being formed between said cover member and said base plate; and several reagents contained in said sample supply pathway, wherein said several reagents include a cholesterol-oxidizing enzyme, cholesterol esterase, an electron mediator, and a buffer having a buffering capacity in an acidic pH range, and wherein said buffer is disposed at a position closer to said sample supply port than any of said cholesterol-oxidizing enzyme, said cholesterol esterase and said electron mediator.

2. The biosensor in accordance with claim 1, wherein said buffer is selected from the group consisting of succinic acid and its salts, citric acid and its salts, phthalic acid and its salts, maleic acid and its salts, and phosphoric acid and its salts.

3. The biosensor in accordance with claim 2, wherein said buffer has a buffering capacity in a pH range of 4 to 6.5.

4. The biosensor in accordance with claim 3, wherein the amount of said buffer is 5 to 1000 nmol per sensor.

5. The biosensor in accordance with claim 4, wherein the amount of said buffer is 20 to 500 nmol per sensor.

6. The biosensor in accordance with claim 1, wherein said cholesterol-oxidizing enzyme and said cholesterol esterase are disposed separately from said electron mediator in said sample supply pathway.

7. The biosensor in accordance with claim 1, wherein said buffer is disposed with said cholesterol-oxidizing enzyme or said cholesterol esterase in said sample supply pathway.

8. The biosensor in accordance with claim 1, wherein said buffer is disposed with said electron mediator in said sample supply pathway.

9. The biosensor in accordance with claim 1, wherein said buffer is disposed separately from said cholesterol-oxidizing enzyme, said cholesterol esterase and said electron mediator in said sample supply pathway, and said buffer is disposed at a position closer to said sample supply port than said cholesterol-oxidizing enzyme, said cholesterol esterase and said electron mediator.

10. The biosensor in accordance with claim 1, further comprising a filter in said sample supply pathway.

11. The biosensor in accordance with claim 10, wherein said filter is disposed at a position close to said sample supply port.

12. The biosensor in accordance with claim 10, wherein said filter carries said buffer.

13. The biosensor in accordance with claim 1, wherein said cholesterol-oxidizing enzyme is cholesterol oxidase.

14. The biosensor in accordance with claim 1, which is designed for measuring a body fluid.

15. The biosensor in accordance with claim 14, wherein said body fluid is blood, plasma, lymph or interstitial fluid.

16. A measuring system including:
(a) a biosensor comprising: an electrically insulating base plate; an electrode system including a working electrode and a counter electrode formed on said base plate; a cover member joined with said base plate to define a sample supply pathway through which a sample solution is introduced from a sample supply port to said electrode system, said sample supply pathway being formed between said cover member and said base plate; and several reagents contained in said sample supply pathway, wherein said several reagents include a cholesterol-oxidizing enzyme, cholesterol esterase, an electron mediator, and a buffer having a buffering capacity in an acidic pH range, and wherein said buffer is disposed at a position closer to said sample supply port than any of said cholesterol-oxidizing enzyme, said cholesterol esterase and said electron mediator;

(b) voltage application means for applying a voltage between said working electrode and said counter electrode; and (c) current detection means for detecting a current flowing between said working electrode and said counter electrode upon application of the voltage.

17. The measuring system in accordance with claim 16, further comprising a display unit for displaying a current detected by said current detection means or a converted value of said current.

18. A method of substrate quantification using a biosensor comprising: an electrically insulating base plate; an electrode system including a working electrode and a counter electrode formed on said base plate; a cover member joined with said base plate to define a sample supply pathway through which a sample solution is introduced from a sample supply port to said electrode system, said sample supply pathway being formed between said cover member and said base plate; and a reagent layer formed in said sample supply pathway, wherein said reagent layer contains a cholesterol-oxidizing enzyme, cholesterol esterase and an electron mediator, said method comprising:

a pretreatment step of mixing a buffer having a buffering capacity in an acidic pH range with the sample solution;

a step of supplying the sample solution subjected to said pretreatment step to said biosensor; and a step of determining a substrate contained in said sample solution in said biosensor.

* * * * *

UNITED STATES PATENT AND TRADEMARK OFFICE
CERTIFICATE OF CORRECTION

PATENT NO.    : 6,821,410 B2                                                Page 1 of 1
DATED         : November 23, 2004
INVENTOR(S)   : Motokazu Watanabe et al.

It is certified that error appears in the above-identified patent and that said Letters Patent is hereby corrected as shown below:

<u>Title page,</u>
Item [56], References Cited, U.S. PATENT DOCUMENTS, change "3,884,784" to
-- 3,884,764 --

Signed and Sealed this

Tenth Day of May, 2005

JON W. DUDAS
*Director of the United States Patent and Trademark Office*